(12) United States Patent
Ahn et al.

(10) Patent No.: US 9,655,805 B2
(45) Date of Patent: May 23, 2017

(54) WALKING ASSIST ROBOT AND CONTROL METHOD THEREOF

(71) Applicant: Samsung Electronics Co., Ltd., Suwon-Si, Gyeonggi-Do (KR)

(72) Inventors: Sung Hwan Ahn, Seoul (KR); Young Do Kwon, Yongin-si (KR); Young Bo Shim, Seoul (KR); Suk June Yoon, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/559,519

(22) Filed: Dec. 3, 2014

(65) Prior Publication Data

US 2015/0196449 A1    Jul. 16, 2015

(30) Foreign Application Priority Data

Jan. 15, 2014   (KR) .................. 10-2014-0004844

(51) Int. Cl.
| | | |
|---|---|---|
| *A61F 2/48* | (2006.01) | |
| *A61H 3/00* | (2006.01) | |
| *A61F 2/68* | (2006.01) | |
| *A61F 5/01* | (2006.01) | |

(Continued)

(52) U.S. Cl.
CPC ................ *A61H 3/00* (2013.01); *A61F 2/68* (2013.01); *A61F 5/01* (2013.01); *A61H 1/024* (2013.01); *A61H 1/0244* (2013.01); *A61H 1/0266* (2013.01); *A61F 2002/6827* (2013.01); *A61F 2002/704* (2013.01); *A61F 2005/0155* (2013.01); *A61H 2201/1215* (2013.01); *A61H 2201/1238* (2013.01); *A61H 2201/164* (2013.01); *A61H 2201/165* (2013.01); *A61H 2201/1628* (2013.01); *A61H 2201/501* (2013.01); *A61H 2201/5007* (2013.01); *A61H 2201/5046* (2013.01); *A61H 2201/5061* (2013.01); *A61H 2201/5069* (2013.01); *A61H 2201/5084* (2013.01); *A61H 2201/5092* (2013.01); *A61H 2201/5097* (2013.01)

(58) Field of Classification Search
CPC ........ A61F 2002/704; A61F 2002/6827; A61F 2/70; A61F 2/68
See application file for complete search history.

(56) References Cited

U.S. PATENT DOCUMENTS

| | | | | |
|---|---|---|---|---|
| 2006/0135883 A1* | 6/2006 | Jonsson | ................ | A61F 2/6607 600/546 |
| 2010/0113980 A1 | 5/2010 | Herr et al. | | |

(Continued)

FOREIGN PATENT DOCUMENTS

| | | |
|---|---|---|
| JP | 2005092820 A | 4/2005 |
| JP | 2012115312 A | 6/2012 |
| KR | 20100059678 A | 6/2010 |

(Continued)

*Primary Examiner* — Jacqueline Woznicki
(74) *Attorney, Agent, or Firm* — Harness, Dickey & Pierce, P.L.C.

(57) ABSTRACT

A control method of a walking assist robot, may include: estimating a wearer's location on a map including walking environment information; determining a walking environment in a direction in which the wearer moves; and selecting a control mode for assisting the wearer's walking according to the walking environment.

16 Claims, 8 Drawing Sheets

(51) Int. Cl.
*A61H 1/02* (2006.01)
*A61F 2/70* (2006.01)

(56) References Cited

U.S. PATENT DOCUMENTS

2010/0324698 A1\* 12/2010 Sverrisson ........... A61B 5/1038
  623/24
2013/0123672 A1   5/2013 Goffer et al.

FOREIGN PATENT DOCUMENTS

KR      101082161 B1   11/2011
KR     20110125899 A   11/2011

\* cited by examiner

WALKING ASSIST ROBOT AND CONTROL METHOD THEREOF

CROSS-REFERENCE TO RELATED APPLICATION

This application claims the benefit of Korean Patent Application No. 2014-0004844, filed on Jan. 15, 2014 in the Korean Intellectual Property Office, the entire disclosure of which is incorporated herein by reference.

BACKGROUND

1. Field

Example embodiments relate to a walking assist robot and a control method thereof. For example, some example embodiments relate to a walking assist robot capable of automatically selecting a walking assist mode according to a walking environment around a wearer, and a control method of the walking assist robot.

2. Description of the Related Art

Walking assist robots have been developed to help and assist people having difficulty in walking in interior and exterior environments. The walking assist robots can be classified into support-type walking assist robots and wearable walking assist robots.

The support-type walking assist robot may determine a user's walking intention to assist the user with walking. The support-type walking assist robot may include a body, a handle bar mounted on the body, and a plurality of wheels provided in the lower part of the body to move the body.

The wearable walking assist robot may be used to help rehabilitation and muscle power enhancement of elderly peoples and patients having low physical strength of lower extremity. The wearable walking assist robot has an exo-skeleton structure such that it can be worn on a user's lower extremity.

SUMMARY

Example embodiments relate to a walking assist robot capable of automatically selecting a walking assist mode according to a walking environment around a wearer, and a control method of the walking assist robot.

Additional aspects of the example embodiments will be set forth in part in the description which follows and, in part, will be obvious from the description, or may be learned by practice of the example embodiments.

Some example embodiments relate to a control method of a walking assist robot.

In some example embodiments, the control method includes: estimating a wearer's location on a map including walking environment information; determining a walking environment in a direction in which the wearer moves; and selecting a control mode for assisting the wearer's walking according to the walking environment.

Some example embodiments relate to a walking assist robot.

In some example embodiments, the walking assist robot includes: a location detector configured to detect a wearer's location on a map including walking environment information; a walking environment determiner configured to determine a walking environment in a direction in which the wearer moves; and a control mode selector configured to select a control mode for assisting the wearer's walking according to the walking environment.

Therefore, since a control mode of the walking assist robot is selected (e.g. automatically) according to a walking environment around a user, usability of the walking assist robot may be improved.

Since an active sensor, such as a laser sensor or a depth camera, for recognizing a walking environment around a user may not be required, cost saving is possible, and power consumption can be reduced.

Since a map including walking environment information is used, a recognition rate for a walking environment may be prevented from deteriorating due to line of sight restriction.

BRIEF DESCRIPTION OF THE DRAWINGS

These and/or other aspects of the example embodiments will become apparent and more readily appreciated from the following description of the embodiments, taken in conjunction with the accompanying drawings of which.

DETAILED DESCRIPTION

Figure 1:
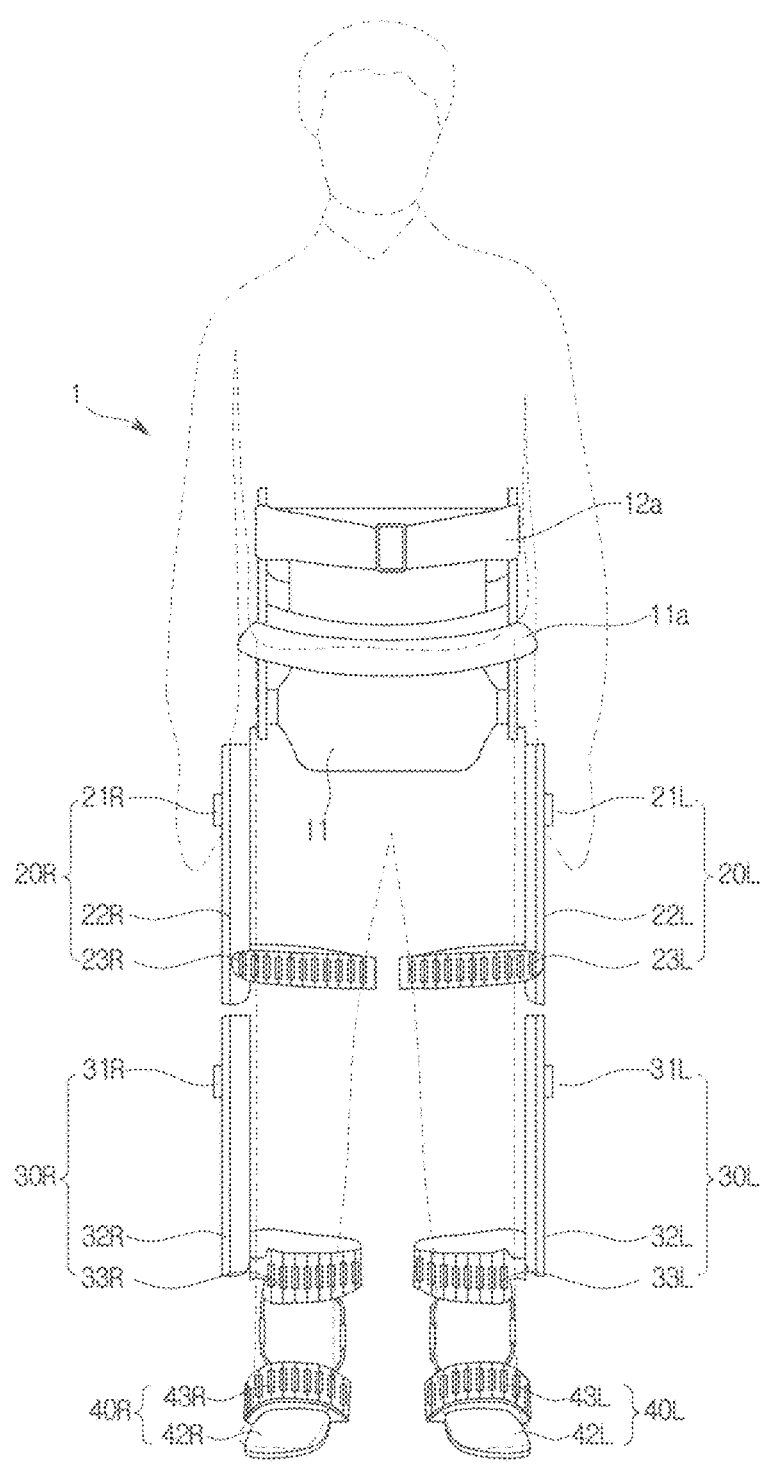
FIG. 1 is a front view of a walking assist robot according to some example embodiments.

Reference will now be made in detail to the example embodiments, some examples of which are illustrated in the accompanying drawings, wherein like reference numerals refer to like elements throughout.

In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, a walking assist robot and a control method thereof according to example embodiments will be described with reference to the appended drawings.

The walking assist robot may include a support-type walking assist robot and a wearable walking assist robot. In the following description, the walking assist robot is assumed to be a wearable walking assist robot, however, example embodiments are not limited thereto.

Figure 2:
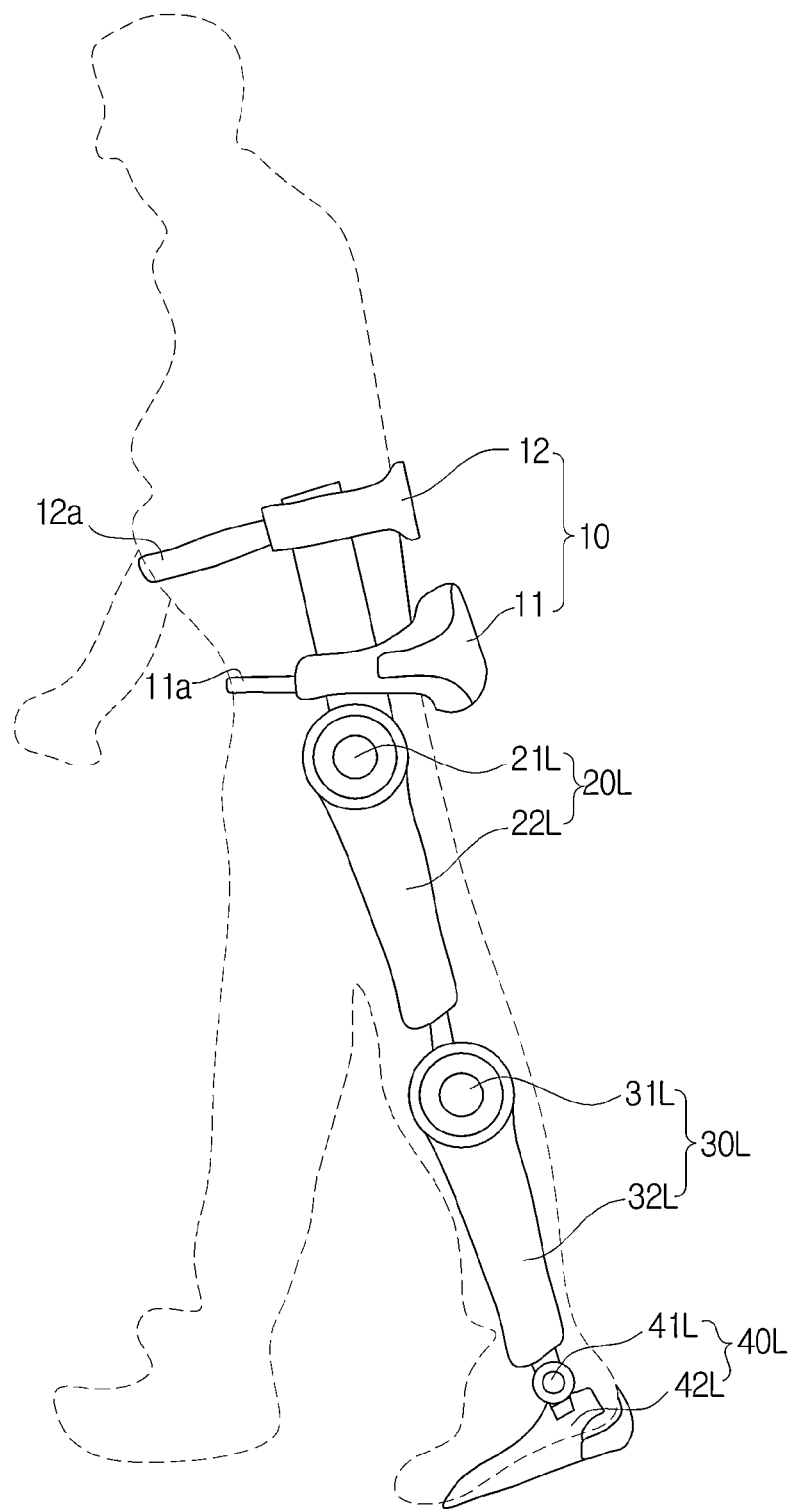
FIG. 2 is a side view of a walking assist robot according to some example embodiments.
Figure 3:
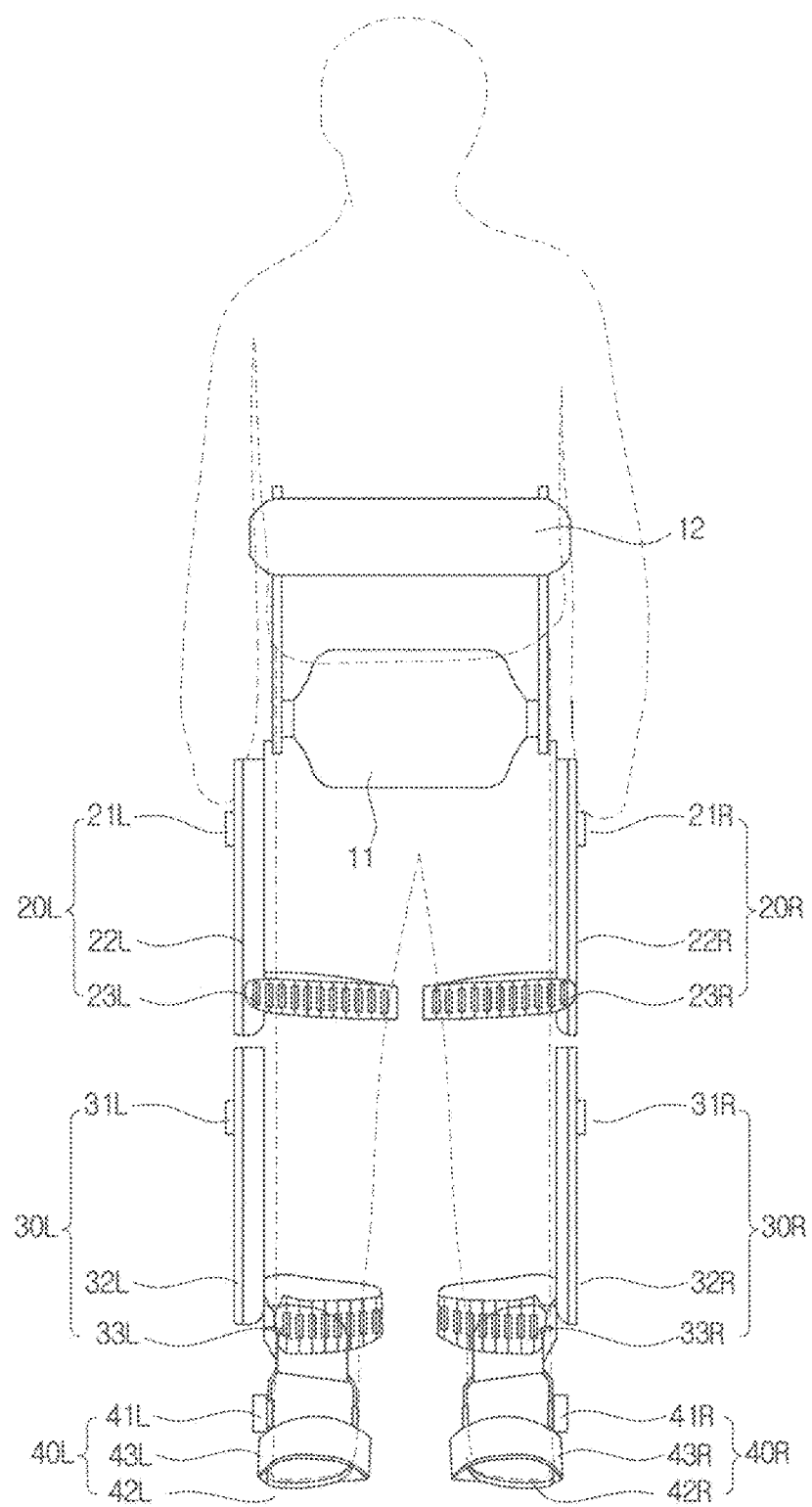
FIG. 3 is a rear view of a walking assist robot according to some example embodiments.

In FIGS. 1, 2, and 3, an example of a wearable walking assist robot 1 that can be worn on a human body is shown. FIG. 1 is a front view of the walking assist robot 1 according to some example embodiments, FIG. 2 is a side view of the walking assist robot 1 according to some example embodiments, and FIG. 3 is a rear view of the walking assist robot 1 according to some example embodiments.

Referring to FIGS. 1 to 3, the walking assist robot 1 may have an exoskeleton structure so that it can be worn on a wearer's left and right legs. The wearer wearing the walking assist robot 1 can perform motions, such as extension, flexion, adduction, abduction, etc. The extension is a motion of extending joints, and the flexion is a motion of bending joints. The adduction is a motion of gathering legs toward the central axis of the body, and the abduction is a motion of spreading legs away from the central axis of the body.

The walking assist robot 1 may include a main body 10, and structures 20R, 20L, 30R, 30L, 40R, and 40L.

The main body 10 may include a housing 11. The housing 11 may accommodate various components therein. The components may include a Central Processing Unit (CPU), a Graphic Processing Unit (GPU), a Printed Circuit Board (PCB), various kinds of storage units, and a power supply.

The CPU may be a micro processor. The micro processor is a processing device in which an Arithmetic Logic Unit (ALU), a register, a program counter, a command decoder, a control circuit, etc. are installed in a silicon chip. If place name information is input from a wearer, the CPU may search for a map related to the place name information in the storage units, and set the wearer's initial location on the map. Thereafter, if the wearer walks so that the wearer's location changes, the CPU may estimate the wearer's current location based on information sensed by various sensors of a sensor unit. Then, the CPU may determine a walking environment around the wearer's current location based on the estimated wearer's current location and the walking environment map. Thereafter, the CPU may select a control mode suitable for the walking environment, and generate control signals for controlling operations of the structures 20R, 20L, 30R, 30L, 40R, and 40L according to the selected control mode.

The GPU is a processing device for processing information related to graphics in the micro processor. The GPU may assist a graphic processing function of the CPU, or may perform graphic processing independently. The GPU may perform image processing on the map found by the CPU. For example, the GPU may display the wearer's initial location on the map, or the wearer's estimated current location on the map.

The PCB is a board on which circuitry is printed, and the CPU, the GPU, and various kinds of storage units may be mounted on the PCB. The PCB may be fixedly mounted on the inner side surface of the housing 11.

The housing 11 may accommodate various kinds of storage units therein. The storage units may include a magnetic disk storage device that magnetizes the surface of a magnetic disk to store data, and a semiconductor memory device that stores data using various kinds of memory semiconductors. According to some example embodiments, the storage units may store a map including walking environment information. The walking environment information may include information about the ground. The information about the ground may be an even ground, an ascent slope, a descent slope, an ascent stair, or a descent stair.

The power supply included in the housing 11 may supply power to various components included in the housing 11 or to the structures 20, 30, and 40.

The main body 10 may further include a waist supporting unit 12 for supporting the wearer's waist. The waist supporting unit 12 may be in the shape of a curved plate to support the wearer's waist.

The main body 10 may further include a fastening unit 11a for fastening the housing 11 on the wearer' hips, and a fastening unit 12a for fastening the waist supporting unit 12 on the wearer's waist. The fastening units 11a and 12a may be implemented with various kinds of means. For example, the fastening units 11a and 12a may be ones of elastic bands, elastic belts, and elastic straps.

The main body 10 may further include an Inertial Measurement Unit (IMU). For example, the IMU may be installed inside or outside the housing 11. More specifically, the IMU may be mounted on a PCB installed in the housing 11. The IMU may include an inertial sensor. The inertial sensor may measure acceleration and angular velocity.

The structures 20, 30, and 40 may include first structures 20R and 20L, second structures 30R and 30L, and third structures 40R and 40L.

The first structures 20R and 20L may support movements of the wearer's hip joints and thighs when the wearer walks. To do this, the first structures 20R and 20L may include first drivers 21R and 21L, first supporting units 22R and 22L, and first fastening units 23R and 23L.

The first drivers 21R and 21R may be disposed to correspond to hip joints of the first structures 20R and 20L, and may generate various magnitudes of rotatory power in predetermined directions. Rotatory power generated by the first drivers 21R and 21L may be applied to the first supporting units 22R and 22L. The first drivers 21R and 21L may rotate within the operating range of a human body's hip joints.

The first drivers 21R and 21L may be driven according to control signals that are provided from the main body 10. The first drivers 21R and 21L may be, for example, ones of motors, vacuum pumps, and hydraulic pumps. However, the first drivers 21R and 21L are not limited to these. In the following description, the first drivers 21R and 21L are assumed to be motors, however, example embodiments are not limited thereto.

Joint angle sensors may be disposed around the first drivers 21R and 21L. The joint angle sensors may detect angles by which the first drivers 21R and 21L rotate with respect to rotation axes.

The first supporting units 22R and 22L may be physically connected to the first drivers 21R and 21L. The first supporting units 22R and 22L may rotate in desired (or, alternatively predetermined) directions according to rotatory power generated by the first drivers 21R and 21L.

The first supporting units 22R and 22L may be designed in various shapes. For example, the first supporting units 22R and 22L may be configured with a plurality of nodes connected to each other. In this case, joints may be disposed between nodes, and the first supporting units 22R and 22L may be bent within a desired (or, alternatively a predetermined) range by the joints. As another example, the first supporting units 22R and 22L may be designed in a bar shape. In this case, the first supporting units 22R and 22L may be made of a flexible material so that the first supporting units 22R and 22L can be bent within a desired (or, alternatively, a predetermined) range.

The first fastening units 23R and 23L may be attached on the first supporting units 22R and 22L, respectively. The first fastening units 23R and 23L function to fasten the first supporting units 22R and 22L on the wearer's thighs. FIGS. 1, 2, and 3 show a case in which the first supporting units 22R and 22L are secured on the outer sides of the wearer's thighs by the first fastening units 23R and 23L. If the first supporting units 22R and 22L move according to rotation of the first drivers 21R and 21L, the wearer's thighs on which the first supporting units 22R and 22L are secured move accordingly in the movement direction of the first supporting units 22R and 22L.

According to some example embodiments, each of the first fastening units 23R and 23L may be implemented with various clamps such as an elastic band, an elastic belt, an elastic strap, or a flexible metal material. FIG. 1 shows a case in which the first fastening units 23R and 23L are chains, however, example embodiments are not limited thereto.

Each of the first structures 20R and 20L may include an IMU. For example, the IMU may be installed in each of the first drivers 21R and 21L. As another example, the IMU may be installed in each of the first supporting units 22R and 22L. As still another example, the IMU may be installed in all of the first drivers 21R and 21L and the first supporting units 22R and 22L. In the following description, a case in which an IMU is installed in each of the first supporting units 22R and 22L will be described as an example, however, example embodiments are not limited thereto.

The second structures 30R and 30L may support movements of the wearer's knee joints and shanks when the wearer walks. To do this, the second structures 30R and 30L may include second drivers 31R and 31L, second supporting units 32R and 32L, and second fastening units 33R and 33L.

The second drivers 31R and 31L may be disposed to correspond to knee joints of the second structures 30R and 30L, and generate various magnitudes of rotatory power in desired (or, alternatively, predetermined directions). Rotatory power generated by the second drivers 31R and 31L may be applied to the second supporting units 22R and 22L. The second drivers 31R and 31L may rotate within the operating range of a human body's knee joints.

The second drivers 31R and 31L may be driven according to control signals that are provided from the main body 10. The second drivers 31R and 31L may be, for example, ones of motors, vacuum pumps, and hydraulic pumps. However, the second drivers 31R and 31L are not limited to these. In the following description, the second drivers 31R and 31L are assumed to be motors, however, example embodiments are not limited thereto.

Joint angle sensors may be disposed around the second drivers 31R and 31L. The joint angle sensors may detect angles by which the second drivers 31R and 31L rotate with respect to rotation axes.

The second supporting units 32R and 32L may be physically connected to the second drivers 31R and 31L. The second supporting units 32R and 32L may rotate in desired (or, alternatively, predetermined) directions according to rotatory power generated by the second drivers 31R and 31L.

The second fastening units 33R and 33L may be attached on the second supporting units 32R and 32L, respectively. The second fastening units 33R and 33L function to fasten the second supporting units 32R and 32L on the wearer's shanks. FIGS. 1, 2, and 3 show a case in which the second supporting units 32R and 32L are secured on the outer sides of the wearer's shanks by the second fastening units 33R and 33L. If the second supporting units 32R and 32L move according to rotation of the second drivers 31R and 31L, the wearer's shanks on which the second supporting units 32R and 32L are secured move accordingly in the movement direction of the second supporting units 32R and 32L.

Each of the second fastening units 33R and 33L may be implemented with one of an elastic band, an elastic belt, an elastic strap, and a metal material.

Each of the second structures 30R and 30L may include an IMU. For example, the IMU may be installed in each of the second drivers 31R and 31L. As another example, the IMU may be installed in each of the second supporting units 32R and 32L. As still another example, the IMU may be installed in all of the second drivers 31R and 31L and the second supporting units 32R and 32L. In the following description, a case in which an IMU is installed in each of the second supporting units 32R and 32L will be described as an example, however, example embodiments are not limited thereto.

The third structures 40R and 40L may support movements of the wearer's ankle joints and related muscles when the wearer walks. To do this, the third structures 40R and 40L may include third drivers 41R and 41L, foot rest units 42R and 42L, and third fastening units 43R and 43L.

The third drivers 41R and 41L may be disposed to correspond to ankle joints of the third structures 40R and 40L, and may be driven according to control signals that are provided from the main body 10. The third drivers 41R and 41L may be motors, like the first drivers 21R and 21L or the second drivers 31R and 31L.

Joint angle sensors may be disposed around the third drivers 41R and 41L. The joint angle sensors may detect angles by which the third drivers 41R and 41L rotate with respect to rotation axes.

The foot rest unit 42R and 42L may be provided to correspond to the locations of the wearer's feet, and physically connected to the third drivers 41R and 41L. Each of the foot rest units 42R and 42L may include at least one sensor. For example, each of the foot rest units 42R and 42L may include a pressure sensor for sensing the wearer's weight. The result of sensing by the pressure sensor may be used to determine whether the wearer wears the walking assist robot 1, whether the wearer stands up, whether the wearer's foot contacts the ground, etc.

The third fastening units 43R and 43L may be connected to the foot rest units 42R and 42L. The third fastening units 43R and 43L may function to fasten the wearer's feet on the foot rest units 42R and 42L.

Each of the third structures 40R and 40L may include an IMU. For example, the IMU may be installed in each of the third drivers 41R and 41L. As another example, the IMU may be installed in each of the foot rest units 42R and 42L. As still another example, the IMU may be installed in all of the third drivers 41R and 41L and the foot rest units 42R and 42L. In the following description, a case in which an IMU is installed in each of the third supporting units 42R and 42L will be described as an example, however, example embodiments are not limited thereto.

Figure 4:
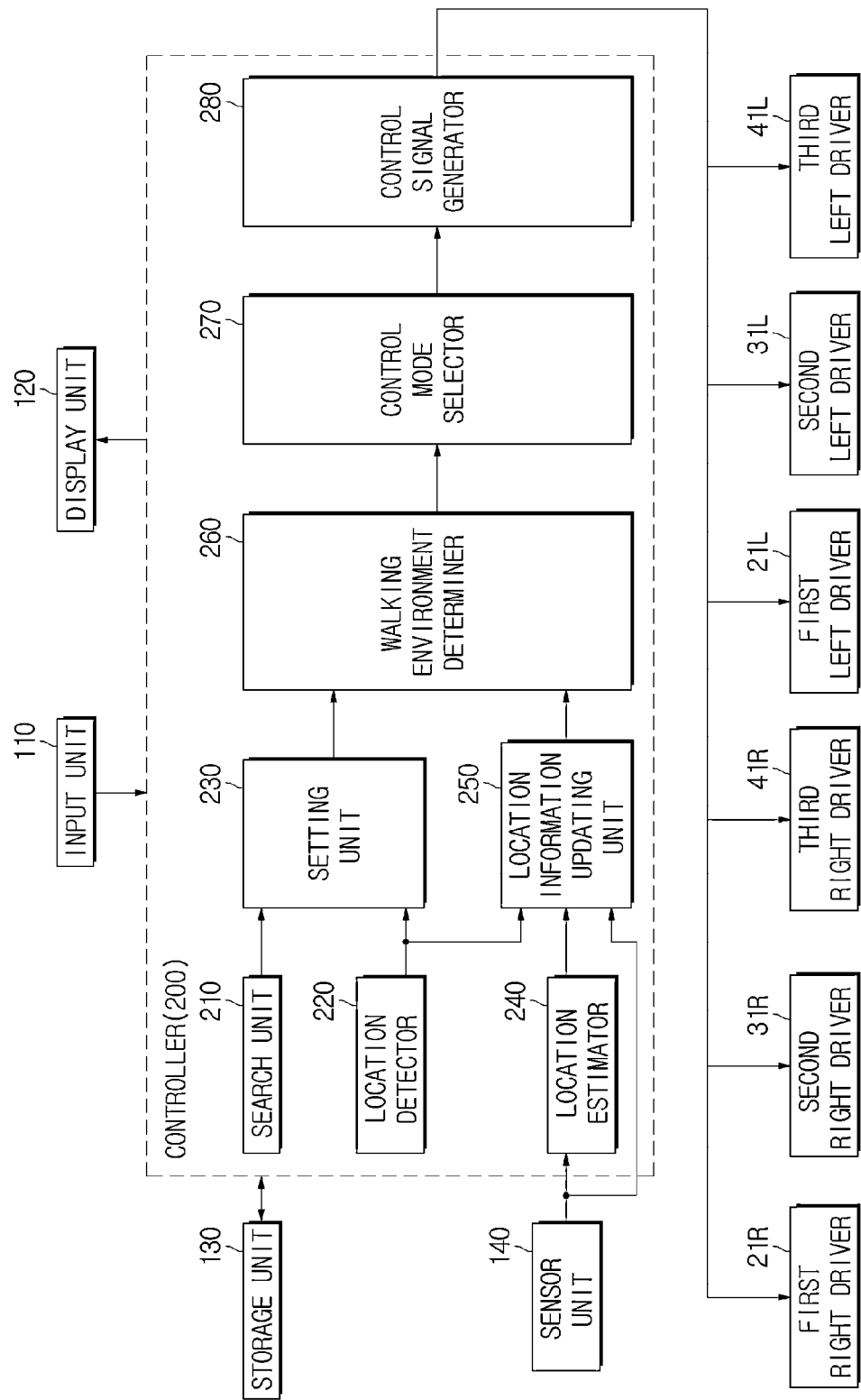
FIG. 4 is a block diagram of a walking assist robot according to some example embodiments.

FIG. 4 is a block diagram of the walking assist robot 1 according to some example embodiments.

Referring to FIG. 4, the walking assist robot 1 may include an input unit 110, a display unit 120, a storage unit 130, a sensor unit 140, a controller 200, and drivers 21R, 31R, 41R, 21L, 31L, and 41L.

The input unit 110 may enable a user to input a command related to operations of the walking assist robot 1. To do this, the input unit 110 may include at least one button. For example, the input unit 110 may include a power button for supplying power to individual components of the walking assist robot 1, a detection execution button to initialize detection of a wearer's location, at least one character input button, and at least one direction button.

The power button may be an on/off button. If the power button is pressed, power may be supplied to various components of the walking assist robot 1, and as discussed below, the controller 200 may detect (e.g. automatically detect) the wearer's location.

The buttons may be implemented by physical buttons, or some of the buttons may be implemented via software. For example, if the input unit 110 and the display unit 120 are integrated into one unit, such as a touch pad or a touch screen, the location detection execution button or the character input button may be displayed as an icon on a desired (or, alternatively, a predetermined) area of the display unit 120.

The display unit 120 may display an operating state of the walking assist robot 1. For example, if a name of a place around the wearer is input through the input unit 110, a map related to the place name may be searched in the storage unit 130, and the display unit 120 may display the found map. The display unit 120 may be separated from the input unit 110, or integrated into the input unit 110.

The storage unit 130 may store a map including walking environment information. The walking environment information may include information about the ground. The information about the ground may be an even ground, an ascent slope, a descent slope, an ascent stair, or a descent stair.

The map including the walking environment information may be generated in advance. For example, the map including the walking environment information may be acquired by moving a mobile robot including a 3Dimensional (3D) laser sensor to acquire 3D point cloud data and projecting the 3D point cloud data onto a 2Dimensional (2D) plane. As another example, the map including the walking environment map information may be acquired by designating information about stairs and slopes from an interior floor plan of a building or house.

Figure 5:
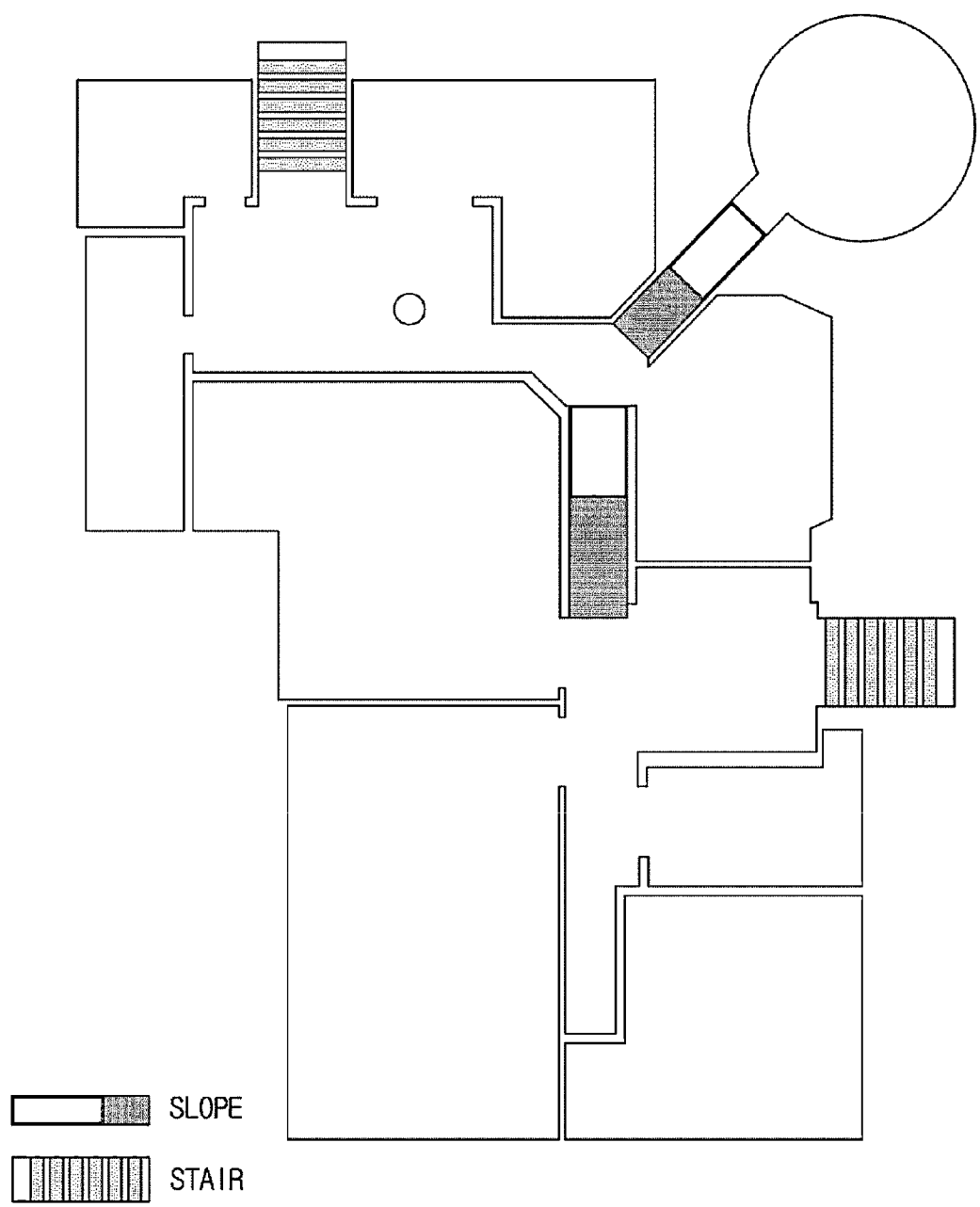
FIG. 5 shows an example of an interior plan including walking environment information.

FIG. 5 shows an example of an interior plan including walking environment information.

As illustrated in FIG. 5, the walking environment information may include an interior plan including information about stairs and information about degrees of slope as walking environment information. A map including walking environment information may be periodically updated based on information received from an external device. In order to update the map, the walking assist robot 1 may further include a communication unit (not shown) for communicating with an external device.

Referring again to FIG. 4, the storage unit 130 may store various data or algorithms needed for operations of the walking assist robot 1, other than the map. For example, the storage unit 140 may store data or algorithms for estimating the wearer's location, and data or algorithms for controlling the walking assist robot 1 according to a control mode. The data for estimating the wearer's location may be kinematic information of the walking assist robot 1. The kinematic information of the walking assist robot 1 may include the size and length of each structure, and a motion model of the walking assist robot 1.

The storage unit 130 may be a nonvolatile memory device, a volatile memory device, a storage medium, or a combination of two or more of the above-mentioned devices.

Figure 6:
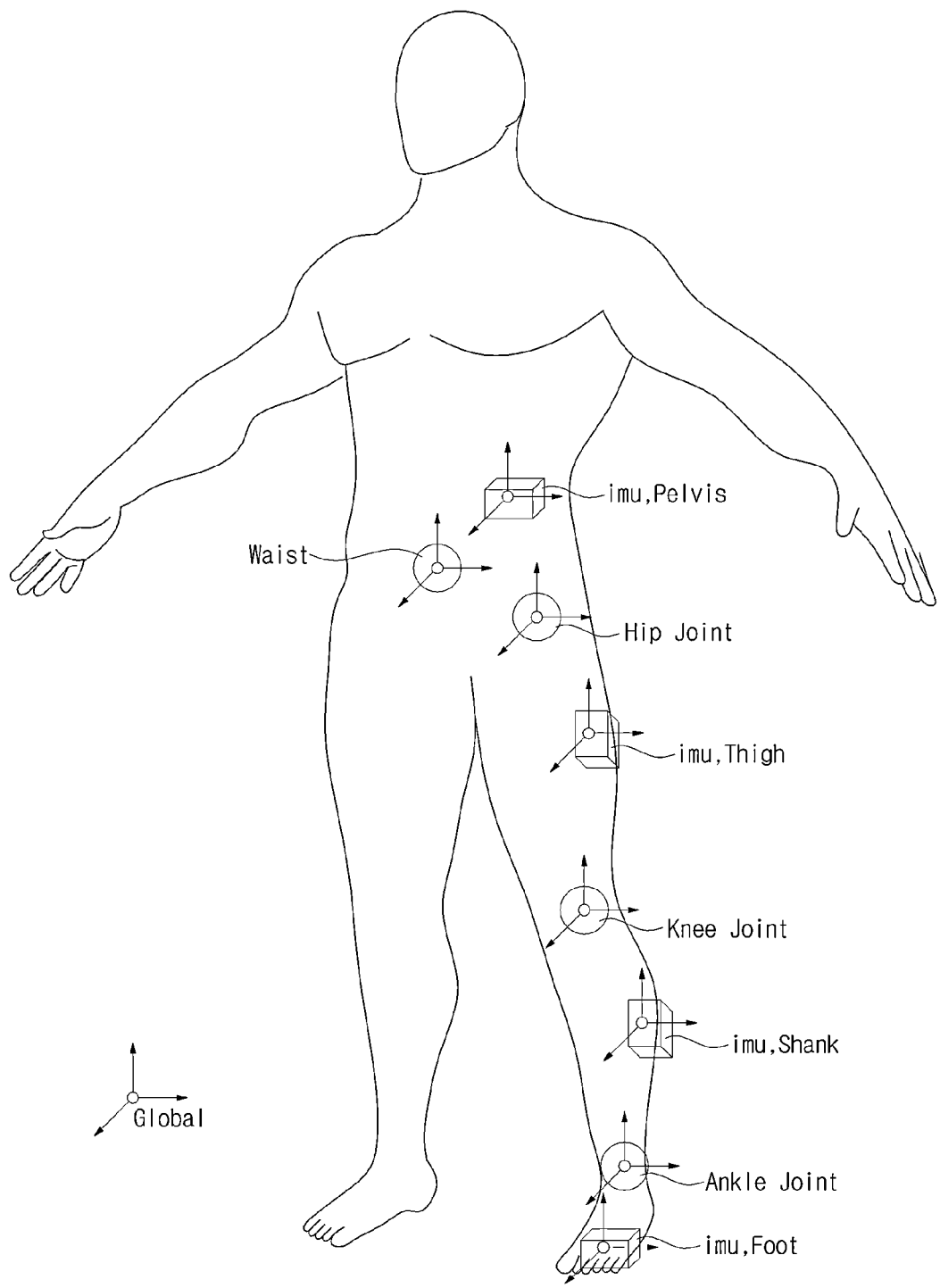
FIG. 6 shows an example of a motion model of a walking assist robot.

FIG. 6 shows an example of a motion model of the walking assist robot 1.

Referring to FIG. 6, inertial sensors may be respectively disposed to correspond to the wearer's pelvis, thighs, shanks, and feet. Also, joint angle sensors may be respectively disposed to correspond to the wearer's waist, hip joints, knee joints, and ankle joints. In FIG. 6, "Global" represents a reference point of the walking assist robot 1. The locations of the inertial sensors, and the relative locations and directions of joints with respect to the inertial sensors may be decided when the walking assist robot 1 is designed. More specifically, a relative location and direction of the waist joint with respect to the inertial sensor disposed to correspond to the pelvis, relative locations and directions of the hip joints with respect to the inertial sensors disposed to correspond to the thighs, relative locations and directions of the knee joints with respect to the inertial sensors disposed to correspond to the shanks, and relative locations and directions of the ankle joints with respect to the inertial sensors disposed to correspond to the feet may be decided when the walking assist robot 1 is designed. The decided values may be stored in the storage unit 130.

Referring again to FIG. 4, the sensor unit 140 may include various kinds of sensors. Although not shown in FIG. 4, the sensor unit 140 may include inertial sensors disposed in the pelvis and the supporting units of the walking assist robot 1, joint angle sensors disposed in the waist supporting unit and the individual joints of the walking assist robot 1, and pressure sensors disposed in the foot rest units 42R and 42L.

Acceleration and angular velocity measured by each inertial sensor may be used to estimate the wearer's location. A joint angle measured by each joint angle sensor, and pressure measured by each pressure sensor may be used to update the estimated location information.

The controller 200 may connect individual components in the walking assist robot 1, and control operations of the individual components.

The controller 200 may include a processor and a memory.

Figure 8:
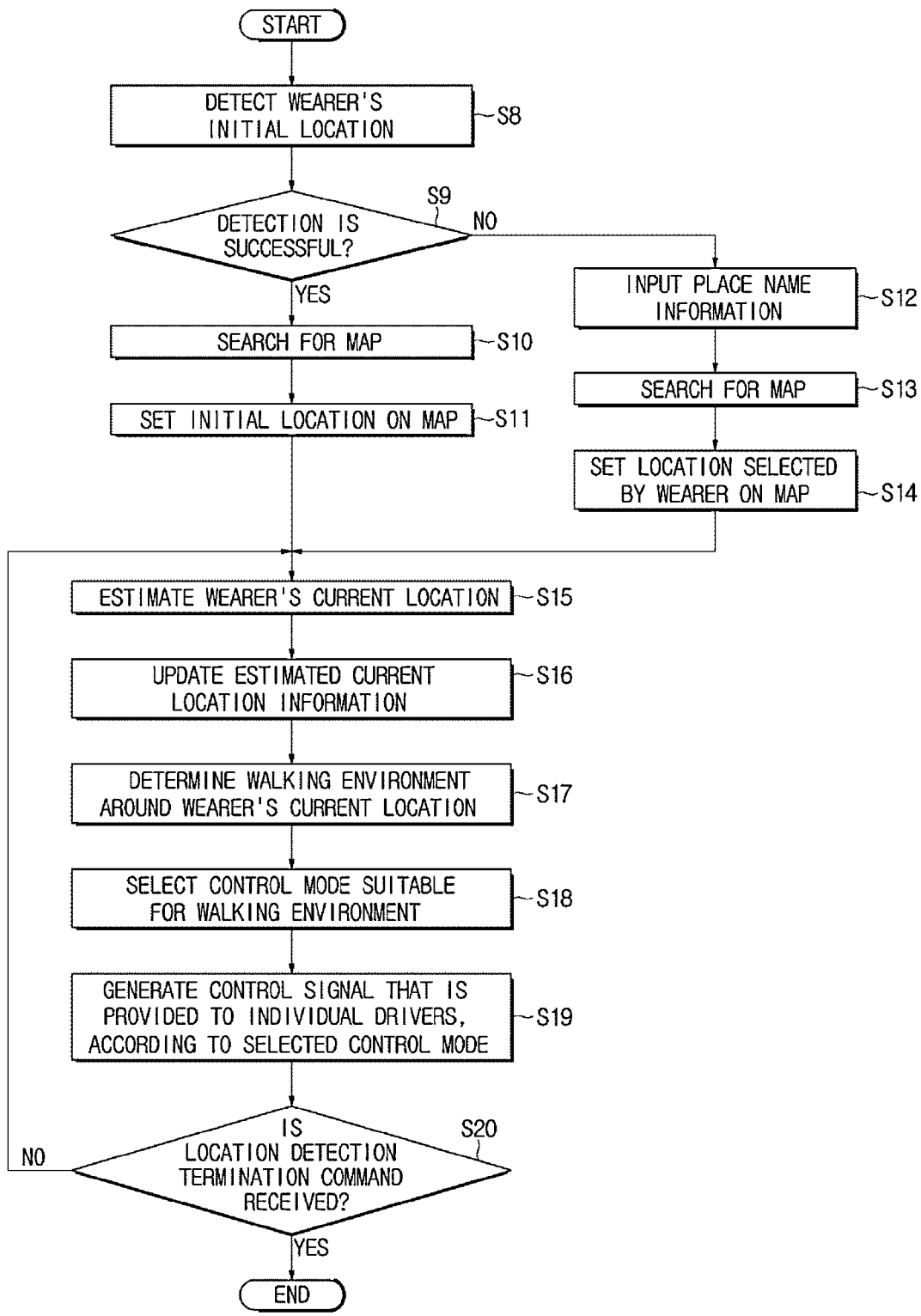
FIG. 8 is a flowchart illustrating a control method of a walking assist robot, according to some example embodiments.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the controller 200 as a special purpose computer to perform the operations illustrated in FIG. 8 such that the controller 200 is configured to estimate the wearer's current location based on information sensed by various sensors of the sensor unit 140 and determine a walking environment around the wearer's current location based on the estimated current location of the wearer and a walking environment map. Further, the controller 200 may select a control mode suitable for the walking environment, and generate control signals for controlling operations of the structures 20R, 20L, 30R, 30L, 40R, and 40L according to the selected control mode.

The controller 200 may include a search unit 210, a location detector 220, a setting unit 230, a location estimator 240, a location information updating unit 250, a walking environment determiner 260, a control mode selector 270, and a control signal generator 280.

For example, the processor of the controller 200 may execute instructions that configure the controller 200 as the search unit 210, the location detector 220, the setting unit 230, the location estimator 240, the location information updating unit 250, the walking environment determiner 260, the control mode selector 270, and the control signal generator 280.

If a wearer's location is detected by the location detector 210, the search unit 210 may search for a map related to the wearer's location in the storage unit 130.

According to other example embodiments, the search unit 21 may search for a map in the storage unit 130, based on a name of a place in which a wearer is located. The place name information may be received through the input unit 110. If the wearer inputs place name information through the input unit 110, the search unit 21 may search for a map related to the place name information in the storage unit 110. The map may be provided to the setting unit 230 which will be described later.

The location detector 220 may detect the wearer's location based on data received from an external device. For example, the location detector 220 may receive data from a plurality of base stations, and detect the wearer's location based on triangulation. According to other example embodiments, the location detector 220 may detect the wearer's location based on satellite signals received from a plurality of satellites. The wearer's location detected by the location detector 220 may be the wearer's initial location. The wearer's initial location may be the wearer's location at a time when a location detection execution button is selected, or at a time when location detection is performed after the wearer moved to another place.

For example, location detection may be performed when a power button included in the input unit 110 is pressed. As another example, location detection may be performed when a location detection execution button included in the input unit 110 is pressed. As still another example, location detection may be automatically performed when the wearer moves to another place. More specifically, location detection may be automatically performed when the wearer moves to another building or to another floor in the same building.

If the wearer's location has been successfully detected, information about the wearer's location may be provided to the search unit 210 and the setting unit 230, as described above. Then, the controller 200 may search the search unit 210 for a map related to the wearer's location, and provide the found map to the setting unit 230. Then, the setting unit 230 may set the wearer's location detected by the location detector 220 on the map found by the search unit 210. If the wearer's location detection fails, the results of the failure may be displayed on the display unit 120. In this case, the wearer may himself or herself input place name information through the input unit 110 to search for a map related to the place name information. Thereafter, if a map related to the place name information is found, the map may be displayed through the display unit 120, and the wearer may set his/her location on the displayed map.

The setting unit 230 may set the wearer's initial location detected by the location detector 220 on the map found by the search unit 210. If the location detector 220 has successfully detected the wearer's location, setting the wearer's initial location on the map may be automatically performed. If the location detector 220 has failed to detect the wearer's location, the wearer may himself or herself set his/her location on the map through the display unit 120.

The location estimator 240 may estimate the wearer's location based on data measured by the inertial sensors of the sensor unit 140. More specifically, if the wearer moves after the wearer's initial location is set on a map, each inertial sensor may measure acceleration and angular velocity according to the wearer's movement. Then, the location estimator 240 may estimate the wearer's current location based on the acceleration and angular velocity measured by each inertial sensor. According to an embodiment, the location estimator 240 may estimate the wearer's location using a Kalman Filter including, as state variables, the locations, velocities, and directions of the inertial sensors, and the locations and directions of the joints included in the walking assist robot 1.

The location information updating unit 250 may update the wearer's estimated current location. This corresponds to update step of the Kalman Filter. For example, the location information updating unit 250 may update the wearer's current location, based on at least one of information about a direction of gravity, information about joint angles measured by joint angle sensors, information about the lengths of supporting units between joints, and information about whether the wearer's feet contact the ground. As another example, the location information updating unit 250 may update the wearer's estimated current location based on information about the wearer's current location detected by the location detector 220. The updated location information may be provided to the walking environment determiner 260.

The walking environment determiner 260 may determine a walking environment in a direction in which the wearer moves, based on the map on which the wearer's initial location is set and the wearer's current location information updated by the location information updating unit 250. For example, the walking environment determiner 260 may determine whether the ground on which the wearer moves is an even ground, an ascent slope, a descent slope, an ascent stair, or a descent stair. The results of the determination may be provided to the control mode selector 270.

The control mode selector 270 may select a control mode suitable for the walking environment determined by the walking environment determiner 260, from among control modes of the walking assist robot 1. The control modes of the walking assist robot 1 may include an even ground mode, an ascent slope mode, a descent slope mode, an ascent stair mode, and a descent stair mode.

The control signal generator 280 may generate control signals that are provided to the individual drivers, according to the selected control mode. For example, if the walking environment determiner 260 determines that the walking environment is an even ground, the control signal generator 280 may generate a control signal for assisting the wearer's walking according to a normal walking cycle. If the walking environment determiner 260 determines that the walking environment is an ascent slope, the control signal generator 280 may generate a control signal for rotating the first right driver 21R or the first left driver 21L with greater rotatory power than in the normal walking cycle according to a degree of slope.

The control signal may be provided to the first driver 21R, the second driver 31R, and the third driver 41R located to the right of the walking assist robot 1, and to the first driver 21L, the second driver 31L, and the third driver 41L located to the left of the walking assist robot 1.

Figure 7:
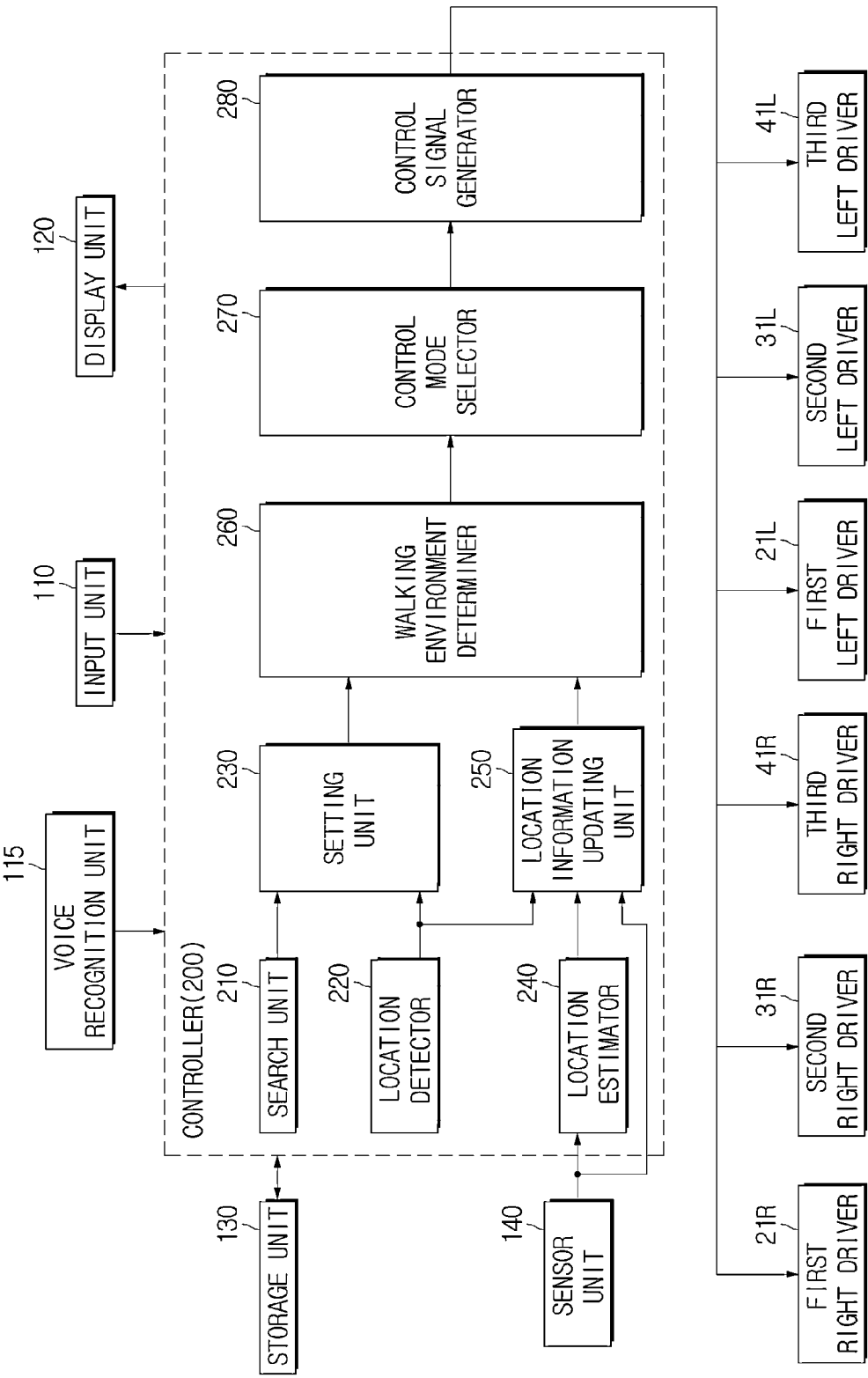
FIG. 7 is a block diagram of a walking assist robot according to other example embodiments.

FIG. 7 is a block diagram of the walking assist robot 1 according to other example embodiments.

Referring to FIG. 7, the walking assist robot 1 may include a voice recognition unit 115 in addition to the input unit 110, the display unit 120, the storage unit 130, the sensor unit 140, the controller 200, and the drivers 21R, 31R, 41R, 21L, 31L, and 41L. That is the walking assist robot 1 shown in FIG. 7 may further include the voice recognition unit 115, compared to the walking assist robot 1 shown in FIG. 4.

The voice recognition unit 115 may recognize a wearer's voice. The voice recognition unit 115 may detect place name information from the wearer's voice, and detect a command related to an operation of the walking assist robot 1, for example, a location detection command, from the wearer's voice.

While FIG. 7 illustrates the voice recognition unit 115 as outside of the controller 200, the processor of the controller 200 may execute instructions that configure the controller 200 as the voice recognition unit 115.

FIG. 8 is a flowchart illustrating a control method of the walking assist robot 1, according to some example embodiments.

Referring to FIGS. 4 and 8, in operation S8, the location detector 220 may detect a wearer's initial location. In some example embodiments, the location detector 220 may automatically detect the wearer's location when power is supplied to the walking assist robot 1 or when the wearer moves to another place. The location detector 220 may detect the wearer's initial location based on data received from an external device. The external device may be a base station, a satellite, or a combination of a base station and a satellite.

In operation S9, the location detector 220 may determine whether the wearer's initial location has been successfully detected. In some example embodiments, the result of the determination may be displayed through the display unit 120, or output in the form of sound or light.

If the location detector 220 determines that the wearer's initial location has been successfully detected, in operations S10 and S11, the setting unit 130 may set the wearer's initial location on a map supplied by the search unit 120.

For example, in operation S10, the search unit 120 may search for a map related to the wearer's initial location in the storage unit 130. In operation S11, the setting unit 230 may set the wearer's initial location on the found map. The map stored in the storage unit 130 may include walking environment information. The map may be an indoor map and an outdoor map. The found map may be displayed through the display unit 120.

If the location detector 220 determines that detection of the wearer's initial location has failed, in operations S12, S13, and S14 the wearer may manually set his/her initial location on the map.

For example, if the location detector 220 determines that detection of the wearer's initial location has failed, the results of the failure may be displayed through the display unit 120. Then, in operation S12, the wearer may input place name information about a place around him/her through the input unit 110. For example, the wearer may input their location to the map using at least one direction button provided on the input unit 110. As another example, if the input unit 110 and the display unit 120 are integrated into one unit, the wearer may input his/her location to the map using a stylus pen or a finger.

If the place name information is input, in operation S13, the search unit 210 may search for a map related to the place name information in the storage unit 130. The found map may be displayed through the display unit 120. Then, in operation S14, the setting unit 230 may set a location selected by the wearer on the found map as the initial location.

If setting the wearer's initial location on the map is completed, the wearer may start walking. If the wearer's location changes according to the wearer's walking, in operation S15, the location estimator 230 may estimate the wearer's current location based on data measured by individual inertial sensors of the walking assist robot 1. The wearer's current location may be estimated using the Kalman Filter including, as state variables, information about the locations, velocities, and directions of the individual inertial sensors, and information about the relative locations and directions of joints with respect to the individual inertial sensors.

The location estimator 230 may estimate the wearer's current location by estimating information associated with joints of the walking assistance robot 1 based on estimated information from inertial sensors. For example, the location estimator 230 may estimate locations, velocities, and directions of the individual inertial sensors at a current time based on accelerations and angular velocities measured by the individual inertial sensors, and estimate locations and directions of the individual joints at the current time based on the estimated locations and directions of the individual inertial sensors and the relative locations and directions of the individual joints with respect to the individual inertial sensors.

In operation S16, the location information updating unit 250 may update (e.g. correct) the wearer's current location information estimated in operation S15.

For example, the location information updating unit 250 may correct the estimated current location information based on at least one of information about a direction of gravity, information about joint angles measured by the joint angle sensors, information about lengths of supporting units between joints, and information about whether the wearer's foot contacts the ground. The current location information estimated in operation S15 may have an error since it has been estimated based on accelerations and angular velocities measured by the inertial sensors. Accordingly, by updating the current location information using the above information, the location information updating unit 250 may acquire a more accurate current location of the wearer.

After the current location information is updated, in operation S17, the walking environment determiner 260 may determine a walking environment in a direction in which the wearer moves based on the map on which the wearer's initial location set and the updated current location information.

If a walking environment in a direction in which the wearer moves is determined, in operation S18, the control mode selector 270 may select a control mode suitable for the walking environment.

For example, if the walking environment determiner 260 determines that the walking environment is an even ground, the control mode selector 270 may select an even ground mode. Likewise, if the walking environment determiner 260 determines that the walking environment is an ascent slope or a descent slope, the control mode selector 270 may select an ascent slope mode or a descent slope mode. Further, if the walking environment determiner 260 determines that the walking environment is an ascent stair or a descent stair, the control mode selector 270 may select an ascent stair mode or a descent stair mode.

If the control mode selector 270 selects a control mode suitable for the walking environment, in operation S19, the control signal generator 280 may generate control signals according to the selected control mode and provide the generated control signals to the individual drivers 21R, 21L, 31R, 31L, 41R, and 41R.

For example, if the control mode selector 270 selects an ascent slope mode, the control signal generator 280 may generate a control signal for rotating the first right driver 21R or the first left driver 21L with greater rotatory power than in a normal walking cycle according to a degree of slope. The control signal may be provided to the individual drivers 21R, 21L, 31R, 31L, 41R, and 41R, and the individual drivers 21R, 21L, 31R, 31L, 41R, and 41R may be driven according to the control signal, thereby assisting walking of the wearer wearing the walking assist robot 1.

In operation S20, the controller 200 may be determined whether a location detection termination command is received. If a location detection termination command is received, the controller 200 may terminate the operation of detecting the wearer's location, and if no location detection termination command is received, the controller 200 may repeatedly perform operations S15 to S19.

Example embodiments have been described above. In the embodiments described above, a part (for example, the controller 200) of components constituting the walking assist robot 1 may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described embodiments, embodiments of the present disclosure can thus be implemented through a special purpose computer configured via computer readable code/instructions in/on a medium, e.g., a computer readable medium, to control at least one processing element to implement any above described embodiment. The medium can correspond to any medium/media permitting the storing and/or transmission of the computer readable code.

The computer-readable code can be recorded on a non-transitory medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

Although a few example embodiments have been shown and described, it would be appreciated by those skilled in the art that changes may be made in these example embodiments without departing from the principles and spirit of the example embodiments, the scope of which is defined in the claims and their equivalents.

What is claimed is:

1. A control method of a walking assist robot including a controller having a processor and a memory, the memory containing computer readable code that, when executed by the processor, configures the controller to perform the control method comprising:
   detecting an initial location of a wearer of the walking assist robot based on information from an external device;
   searching the memory for a map related to the initial location of the wearer, the map including walking environment information;
   setting the initial location of the wearer on the searched map;
   reading, from the memory, kinematic information associated with the walking assist robot;
   estimating a current location of the wearer on the searched map by applying the kinematic information associated with the walking assist robot into an algorithm;
   updating the estimated current location of the wearer based on data measured by a plurality of sensors;
   determining a walking environment in a direction in which the wearer moves based on the map on which the initial location of the wearer is set and the updated current location of the wearer; and
   selecting one of a plurality of control modes of the walking assistance robot according to the walking environment.

2. The control method according to claim 1, wherein the walking environment information includes information about the ground.

3. The control method according to claim 2, wherein the information about the ground includes at least one of whether the ground is even, an ascent slope, a descent slope, an ascent stair, a descent stair, and contains an obstacle.

4. The control method according to claim 1, further comprising:
attempting to automatically detect the initial location of the wearer; and
if the attempting is unable to automatically detect the initial location then,
receiving a first input from the wearer, the first input indicating a place name,
searching the memory for a map related to the place name,
receiving a second input from the wearer, the second input indicating the initial location on the searched map, and
setting the initial location input by the wearer on the searched map.

5. The control method according to claim 4, wherein the receiving the first input from the wearer comprises:
receiving a voice command from the wearer and recognizing the place name from the voice command.

6. The control method according to claim 1, wherein the walking assist robot includes one or more inertial sensors and one or more joints, and the estimating the current location of the wearer comprises:
estimating the current location of the wearer using a Kalman Filter, the Kalman Filter having as state variables locations, velocities, and directions of the one or more inertial sensors, and relative locations and relative directions of the one or more joints with respect to the inertial sensors.

7. The control method according to claim 1, further comprising:
detecting the initial location of the wearer based on data received from an external device.

8. The control method according to claim 7, wherein the determining a walking environment comprises:
determining the walking environment at the updated current location of the wearer.

9. The control method according to claim 7, wherein the external device includes at least one of base stations and satellites.

10. The control method according to claim 1, further comprising:
generating a control signal according to the selected control mode; and
controlling at least one driver of the walking assist robot based on the control signal.

11. A walking assist robot comprising:
a controller including a processor and a memory, the memory containing computer readable code that, when executed by the processor, configures the controller to,
detect an initial location of a wearer of the walking assist robot based on information from an external device,
search the memory for a map related to the initial location of the wearer, the map including walking environment information,
set the initial location of the wearer on the searched map,
read, from the memory, kinematic information associated with the walking assist robot,
estimate a current location of the wearer on the searched map by applying the kinematic information associated with the walking assist robot into an algorithm,
update the estimated current location of the wearer based on data measured by a plurality of sensors,
determine a walking environment in a direction in which the wearer moves based on the map on which the initial location of the wearer is set and the updated current location of the wearer, and
select one of a plurality of control modes of the walking assistance robot according to the walking environment.

12. The walking assist robot according to claim 11, wherein if the controller is unable to detect the initial location of the wearer, the controller is configured to,
receive first input from the wearer, the first input indicating a place name,
search the memory for a map related to the place name,
receive second input from the wearer, the second input indicating the initial location on the searched map, and
set the initial location input by the wearer on the searched map.

13. The walking assist robot according to claim 12, wherein the controller is configured to detect the initial location of the wearer based on data received from an external device.

14. The walking assist robot according to claim 12, further comprising:
a voice recognition unit configured to recognize the place name from a voice command from the wearer.

15. The walking assist robot according to claim 11, wherein the walking assist robot further comprises:
one or more inertial sensors and one or more joints, and wherein
the controller is configured to estimate the current location of the wearer using a Kalman Filter, the Kalman Filter including as state variables, information about locations, velocities, and directions of the inertial sensors, and information about relative locations and relative directions of the joints with respect to the inertial sensors.

16. The walking assist robot according to claim 15, wherein the controller is configured to,
estimate locations, velocities, and directions of the inertial sensors at a current time based on accelerations and angular velocities measured by the inertial sensors, and
estimate locations and directions of the joints at the current time, based on the estimated locations and the estimated directions of the inertial sensors and relative locations and relative directions of the joints with respect to the inertial sensors.

* * * * *